United States Patent [19]

Grundei

[11] Patent Number: 4,826,501
[45] Date of Patent: May 2, 1989

[54] BREAST PROSTHESIS

[75] Inventor: Hans Grundei, Lübeck, Fed. Rep. of Germany

[73] Assignee: S + G Implants GmbH, Lübeck, Fed. Rep. of Germany

[21] Appl. No.: 153,842

[22] PCT Filed: May 6, 1987

[86] PCT No.: PCT/DE87/00197
 § 371 Date: Jan. 8, 1988
 § 102(e) Date: Jan. 8, 1988

[87] PCT Pub. No.: WO87/06818
 PCT Pub. Date: Nov. 19, 1987

[30] Foreign Application Priority Data

May 9, 1986 [DE] Fed. Rep. of Germany ....... 3615726

[51] Int. Cl.$^4$ ............................................. A61F 2/12
[52] U.S. Cl. ............................................ 623/8; 623/7
[58] Field of Search ........................................ 623/7, 8

[56] References Cited

U.S. PATENT DOCUMENTS

| 2,698,436 | 6/1951 | Bernhardt | 623/7 |
| 3,852,833 | 12/1974 | Köneke et al. | 623/7 |
| 4,199,825 | 4/1980 | Knoche | 623/7 |
| 4,356,573 | 11/1982 | Knoche | 623/7 |
| 4,676,795 | 6/1987 | Grundei | 623/8 |

Primary Examiner—Richard J. Apley
Assistant Examiner—Joe H. Cheng
Attorney, Agent, or Firm—Balogh, Osann, Kramer, Dvorak, Genova & Traub

[57] ABSTRACT

The breast prosthesis consists of an elastically deformable envelope filled at least partly with an inert flowable mass. The shape of said envelope imitates that of the breast and its sidewall, facing the thorax, has a concave form. The prosthesis is provided with at least one transverse through-duct open at its ends, in which is located a non-return valve allowing air to flow only from the inside outwards.

7 Claims, 1 Drawing Sheet

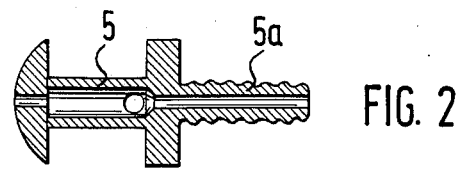
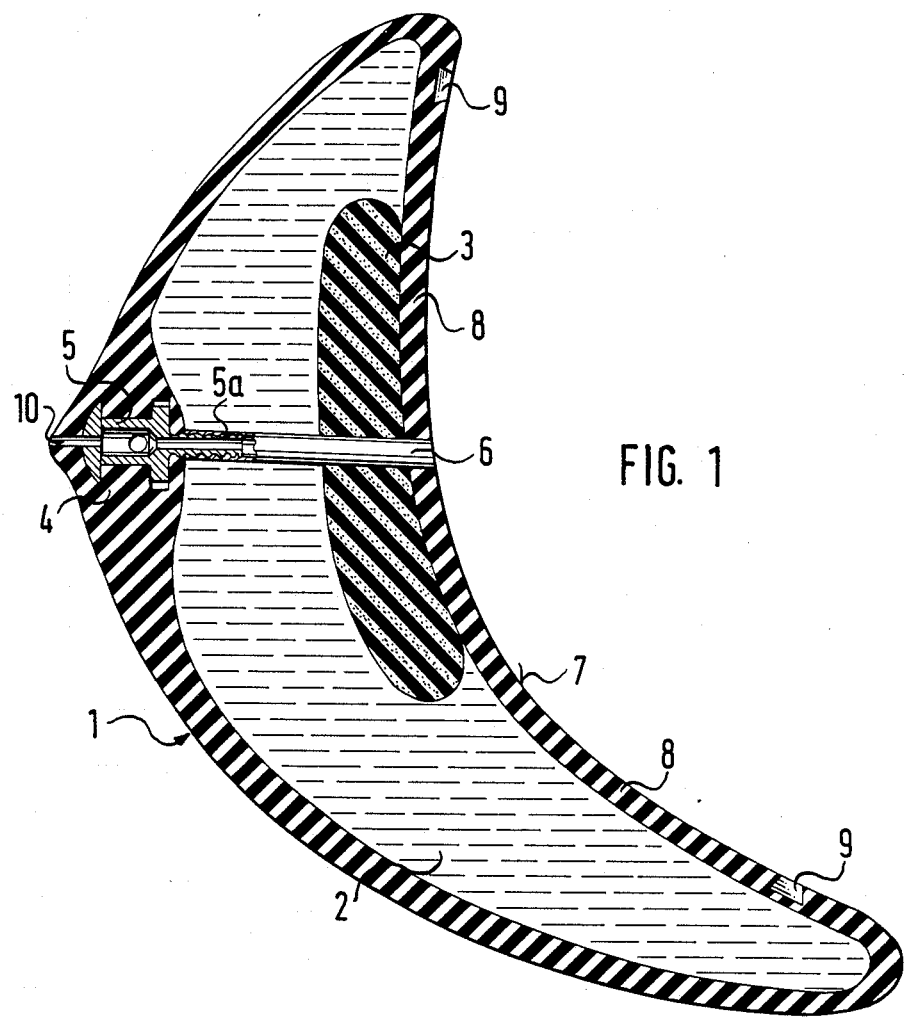

BREAST PROSTHESIS

BACKGROUND OF THE INVENTION

1. Field of the Invention

The invention relates to a breast prosthesis consisting of an elastically deformable envelope which is at least partially filled with a sluggishly flowing substance. The shape of the prosthesis simulates the natural shape of the breast, while that surface of the envelope, which is directed towards the thorax, has a substantially concavely curved shape.

2. Description of the Related Art

Breast prostheses of the aforementioned kind are known from DE-OS No. 34 40 960 (U.S. Pat. No. 4,676,795). The known breast prostheses can, upon movement of the body, move swinging like a normal breast. Even when a part of the interior of the envelope is replaced by an elastically deformable, porous formed member, e.g. made of natural or synthetic foam, the weight of the breast prosthesis is still considerable. This weight has to be absorbed by a brassière, the supports of which lead to constrictions on the shoulders of the wearer. In this respect, the proper fitting of the prosthesis on the body of the chest cannot be affected.

The problem of the invention consists in providing for a breast prosthesis, on the one hand a secure specific seat on the body and in so designing the prosthesis that the body of the wearer at least partially directly absorbs the weight of the prosthesis.

SUMMARY OF THE INVENTION

In accordance with the invention, this problem is solved by providing at least one duct extending through the body of the prosthesis, which duct connects apertures on the inner and outer surfaces of the envelope and that a valve, which allows a flow of air only from the inside outwardly, is arranged in the duct.

As a result of this solution, the wearer needs to press the prosthesis only once or several times against the chest and then release it again, so that, when between the prosthesis and the chest a vacuum arises, the peripheral edge of the prosthesis acts to apply a sealing action against the thorax. Thereby a secure position of the prosthesis is achieved and the weight of the prosthesis, at least part of the same, is sustained directly by the thorax.

The duct is, in accordance with a further development, formed by a tube which is connected to the valve which is provided in the envelope. In this respect, the valve lies in the nipple region of the envelope which is appropriately thickened, and is for example vulcanized in the envelope.

It is advantageous for the prosthesis to be provided, on the surface facing the chest, in the vicinity of the peripheral edge with an encircling groove which is filled with a sealing compound which adheres to the thorax.

In order to guarantee the creation of an underpressure in the region between the prosthesis and the surface of the thorax, it is necessary that the wall of the prosthesis envelope, which faces the thorax, is of a stable shape in design and spatially so curved that a cavity is formed between the prosthesis and the thorax. After the prosthesis has been compressed once or several times, the air will after each release of the prosthesis flow out of the space between the prosthesis and the thorax by way of the check valve. In this way, in this space through the return of the prosthesis into the initial shape an underpressure is generated by which the prosthesis is secured in position at its applied location and in which respect the weight is at least partially supported by the thorax. Thus, a brassière has to absorb a slight weight and forms an additional retention security.

BRIEF DESCRIPTION OF THE DRAWINGS

The invention will be explained hereinunder with reference to the drawings, in which an exemplified embodiment of a breast prosthesis is shown and in which:

FIG. 1 shows a horizontal section through the breast prosthesis in accordance with the invention;

FIG. 2 shows, on an enlarged scale, a section through the check valve installed in the axial region of the prosthesis.

DESCRIPTION OF THE PREFERRED EMBODIMENT

The prosthesis as a replacement for an amputated breast consists of an inherently stable, elastic envelope 1, which is matched in shape to the natural breast. This envelope 1 advantageously consists of a vulcanized silicon rubber and is filled with a sluggishly flowing substance in space 2, for example a partly-vulcanized silicon rubber gel. The space 2 to be filled can, to reduce weight, be partially occupied by a natural or synthetic foam body 3.

The outer wall of the envelope is thickened in the nipple region 4, and a check valve 5 is vulcanized into this thickened weall. This check valve 5, shown enlarged in FIG. 2, is provided with a branch 5a which extends freely into the envelope space 2 and onto which is slipped the end of a tube 6 which extends transversely through the prosthesis and which ends flush with the surface 7, directed towards the chest, of the wall 8 of the envelope. The end of the tube 6 which faces the chest may be widened in a trumpet-shaped manner.

The wall 8 of the envelope which faces the chest is provided in the vicinity of the peripheral edge with a groove 9, for example an undercut groove, into which is filled a compound, for example an appropriately prepared silicon rubber gel, which adheres in sealing manner to the thorax. The surface 8 of the envelope is so curved in an inherently stable manner that, when the prosthesis is applied to the chest, a cavity is formed between the wall 8 of the envelope and the surface of the chest. So that the air in this cavity, after the prosthesis has been applied against the surface of the chest, can be vented by way of the tube 6 and the check valve 5 into the outside air. The wall 8 is provided with a pierced hole 10 in the region of the valve 5.

The breast prosthesis is so placed against the thorax that the sealing compound in the edge region of the wall 8 abuts against the thorax, so that the prosthesis is thereby held adheringly by the thorax. Then, the prosthesis, as a whole, is pressed by manual pressure against the thorax, so that in this way the trapped air at least partially escapes outwardly out of the cavity between the wall 8 of the envelope and the thorax by way of the tube 6, the check valve 5 and the pierced hole 10. When the prosthesis is released, the deformed prosthesis attempts, as a result of the elasticity of its envelope, to assume its initial position again. As a result, the space between the wall 8 of the envelope and the thorax is enlarged. In this space an underpressure arises, i.e. the ball of the check valve 5 is applied to its seat, so that the underpressure is maintained in the aforesaid space. This procedure may be repeated several times, until the desired underpressure is achieved in the space between the wall 8 of the envelope and the thorax. Thus the prosthesis is seated securely at the correct position and the weight of the prosthesis is thus at least partially supported by the thorax itself, so that the brassière being used and the supports thereof are relieved.

I claim:

1. A breast prosthesis, consisting of an elastically deformable envelope which is at least partially filled with a sluggishly flowing substance and the shape of which conforms to the natural shape of the breast, one surface of the envelope, which is directed towards the thorax, has substantially a concavely curved shape, including at least one duct extending through a body of the prosthesis and connecting apertures on inner and outer surface of the envelope, a valve incorporated in the duct to allow flow of air from the inside of said surface outwardly for venting into atmospheric air, and a region of the envelope simulating a nipple, is a thickened material which supports the valve for securing against axial displacement.

2. A breast prosthesis according to claim 1, characterized in that the duct is formed by a flexible tube which is connected to the valve inserted in the envelope.

3. A breast prosthesis according to claim 1, characterized in that the duct has an end directed to the thorax, which end widens in a trumpet-shaped manner.

4. A breast prosthesis according to claim 1, characterized in that an encircling seal is provided in the vicinity of an outer wall of the envelope which is directed to the thorax.

5. A breast prosthesis according to claim 4, characterized in that the seal is embedded in a groove in said wall facing the thorax and consists of an adhesive material.

6. A breast prosthesis according to claim 1, characterized in that said wall of the envelope which faces the thorax is of stable shape and spatially curved in unloaded state, in such a way that upon placing of the prosthesis on the thorax, a gap and free space is formed between said wall of the envelope and the thorax.

7. A breast prosthesis as a replacement for an amputated breast, consisting of an envelope made of a vulcanized silicon rubber which conforms to the shape of the breast and which is at least partially filled with a partly vulcanized silicon rubber, characterized in that the envelope is provided, in the nipple region, with a thickened wall in which there is vulcanized a check valve which allows a flow of trapped air from the inside of the prosthesis in an outward direction, said check valve has a branch extending from the thickened wall of the envelope and connected to a tube which ends with a free outlet on a side of the envelope facing to the thorax, said side being provided with an encircling edge groove which is filled with a sealing compound for abutting against the thorax.

* * * * *